US011883410B2

(12) United States Patent
Inada et al.

(10) Patent No.: US 11,883,410 B2

(45) Date of Patent: Jan. 30, 2024

(54) PREVENTATIVE AND THERAPEUTIC AGENTS FOR SARCOPENIA

(71) Applicants: NATIONAL UNIVERSITY CORPORATION TOKYO UNIVERSITY OF AGRICULTURE AND TECHNOLOGY, Fuchu (JP); TAIHO PHARMACEUTICAL CO., LTD., Tokyo (JP)

(72) Inventors: Masaki Inada, Fuchu (JP); Daisuke Kajiwara, Tsukuba (JP)

(73) Assignees: National University Corporation Tokyo University of Agriculture and Technolgy, Fuchu (JP); Taiho Pharmaceutical Co., Ltd., Tokyo (JP)

( * ) Notice: Subject to any disclaimer, the term of this patent is extended or adjusted under 35 U.S.C. 154(b) by 342 days.

(21) Appl. No.: 17/047,436

(22) PCT Filed: Apr. 18, 2019

(86) PCT No.: PCT/JP2019/016579

§ 371 (c)(1),
(2) Date: Oct. 14, 2020

(87) PCT Pub. No.: WO2019/203296

PCT Pub. Date: Oct. 24, 2019

(65) Prior Publication Data

US 2021/0161908 A1 Jun. 3, 2021

(30) Foreign Application Priority Data

Apr. 19, 2018 (JP) ................................ 2018-080834
Jul. 11, 2018 (JP) ................................ 2018-131371

(51) Int. Cl.
*A61K 31/5377* (2006.01)
*A61P 21/06* (2006.01)

(52) U.S. Cl.
CPC .......... *A61K 31/5377* (2013.01); *A61P 21/06* (2018.01)

(58) Field of Classification Search
CPC ............ A61K 31/5377; A61K 31/4184; A61K 31/454; A61P 21/00; A61P 21/06
See application file for complete search history.

(56) References Cited

U.S. PATENT DOCUMENTS 7,238,718 B2 7/2007 Urade et al.
7,951,956 B2 5/2011 Urade et al.
8,765,750 B2 * 7/2014 Urade .................. C07D 403/14 514/235.8
8,865,714 B2 * 10/2014 Urade .................. C07D 401/14 514/235.8
9,062,035 B2 6/2015 Urade et al.
2005/0272767 A1 * 12/2005 Urade .................... A61K 31/47 514/310
2009/0281098 A1 * 11/2009 Urade ................ A61K 31/5377 514/234.5
2011/0319413 A1 12/2011 Urade et al.
2012/0309760 A1 12/2012 Urade et al.
2014/0128394 A1 5/2014 Urade et al.

FOREIGN PATENT DOCUMENTS

JP 2005-119984 A 5/2005
WO 95/01350 A1 1/1995
WO 2007/007778 A1 1/2007
WO 2010/104024 A1 9/2010
WO 2011090062 A1 7/2011
WO 2017150228 A1 9/2017

OTHER PUBLICATIONS

Pedro Veliça, Farhat L. Khanim, Chris M. Bunce, Prostaglandin D2 inhibits C2C12 myogenesis, Molecular and Cellular Endocrinology, vol. 319, Issues 1-2, 2010, pp. 71-78, ISSN 0303-7207, https://doi.org/10.1016/j.mce.2010.01.023. (Year: 2010).*
Dalle S, Rossmeislova L, Koppo K. The Role of Inflammation in Age-Related Sarcopenia. Front Physiol. Dec. 12, 2017;8:1045. doi: 10.3389/fphys.2017.01045. PMID: 29311975; PMCID: PMC5733049. (Year: 2017).*
Trappe TA, Liu SZ. Effects of prostaglandins and COX-inhibiting drugs on skeletal muscle adaptations to exercise. J. Appl. Physiol. (1985). Sep. 2013;115(6):909-19. PMID: 23539318. (Year: 1985).*
Extended European Search report dated Dec. 13, 2021 for EP Pat Appln. No. 19789246.6, 8 pages.
Mohri et al., "Inhibition of Prostaglandin D Synthase Suppresses Muscular Necrosis", The American Journal of Pathology, vol. 174, No. 5, 2009, pp. 1735-1744.
Tanaka et al., "Novel inhibitor of hematopoietic prostaglandin D synthase improves the muscle disorder in an experimental model of Duchenne muscular dystrophy", Neuromuscular Disorders, vol. 24, No. 9-10, 2014, p. 821.
Urade, "Orphan drug development for Duchenne musclar dystrophy by protein crystallization in space", International Astronautical Congress, 2016, abstract.
Office Action dated Dec. 17, 2021 for TW Pat. Appln. No. 108113676, 11 pages.
Merlini et al., "Pathophysiological mechanisms of sarcopenia in aging and in muscular dystrophy: a translational approach.", Frontiers in aging neuroscience 7 (2015): 153., pp. 1-3.
Urade et al., "Inhibition of hematopoietic prostaglandin D synthase decelerates the progression of Duchenne muscular dystrophy", Journal of Clinical and Experimental Medicine, 2016, vol. 259, No. 1, pp. 37-42.
Kajiwara et al., "Role of hematopoietic prostaglandin D synthase in biphasic nasal obstruction in guinea pig model of experimental allergic rhinitis", European Journal of Pharmacology, 2011, vol. 667, pp. 389-395.

(Continued)

*Primary Examiner* — Theodore R. Howell
(74) *Attorney, Agent, or Firm* — Rothwell, Figg, Ernst & Manbeck, P.C.

(57) ABSTRACT

This invention relates to a preventive and/or therapeutic agent for sarcopenia, comprising a prostaglandin D2 production inhibitor as an active ingredient.

6 Claims, 7 Drawing Sheets

(56) References Cited

OTHER PUBLICATIONS

Baumgartner et al., "Epideminology of Sarcopenia among the Elderly in New Mexico", American Journal of Epidemiology, 1998, vol. 147, No. 8, pp. 755-763.
Thuy-Tien Dam et al., An Evidence-Based Comparison of Operational Criteria for the Presence of Sarcopenia, J Gerontol A Biol Sci Med Sci, 2014, vol. 69, No. 5, pp. 584-590.
International Search Report cited in PCT/JP2019/016579 dated Jun. 25, 2019, 2 pages.

* cited by examiner

| Tail-suspension | Compound No. (0.01 %) | Rate of increase |
| --- | --- | --- |
| - | - | 100.0 |
| + | - | 0.0 |
| + | (1) | 26.3 |
| + | (2) | 6.4 |
| + | (3) | 33.3 |
| + | (4) | 33.3 |
| + | (5) | 28.0 |

| Tail-suspension | Compound No. (0.01 %) | Rate of increase |
|---|---|---|
| — | — | 100.0 |
| + | — | 0.0 |
| + | (1) | 34.2 |
| + | (2) | 24.9 |
| + | (3) | 32.4 |
| + | (4) | 33.8 |
| + | (5) | 32.7 |

PREVENTATIVE AND THERAPEUTIC AGENTS FOR SARCOPENIA

CROSS REFERENCE TO RELATED APPLICATION

This application is a 35 U.S.C. 371 National Phase Entry Application from PCT/JP2019/016579, filed Apr. 18, 2019, which claims the benefit of Japanese Patent Application Nos. 2018-080834 filed on Apr. 19, 2018 and 2018-131371 filed on Jul. 11, 2018, the disclosures of which are incorporated herein in their entirety by reference.

TECHNICAL FIELD

The present invention relates to a preventive and/or therapeutic agent for sarcopenia.

TECHNICAL FIELD

Sarcopenia is a disease characterized by progressive and systemic skeletal muscle mass loss and muscle strength loss, occurring in approximately 30% of American males and females over the age of 60, and 50% of those over the age of 80 (Non-patent Literature (NPL) 1). Sarcopenia is believed to cause mobility impairment in 2 to 5% of the elderly (NPL 2). Muscle mass loss and muscle strength loss in the elderly often occur as diminished physical functions, resulting in a reduction in quality of life and an increase in risk of adverse health events (e.g., falls and post-fall fractures).

Sarcopenia includes primary (age-related) sarcopenia with no apparent cause other than aging, and secondary sarcopenia with one or more apparent causes other than aging. Disuse muscle atrophy, which occurs when muscle is not used for a long period of time due to hospitalization etc., is included in secondary sarcopenia.

There is no approved drug for treating sarcopenia at present. With an increase in the number of the patients in an aging society, the creation of therapeutic drugs has been required.

PTL 1, PTL 2, and PTL 3 disclose prostaglandin D2 production inhibitors, such as 4-{(1-methyl-1H-pyrrol-2-yl)carbonyl}-N-[4-{4-(4-morpholinylcarbonyl)-1-piperidinyl}phenyl]-1-piperazine carboxamide, N-methoxy-N-methyl-4-(5-benzoylbenzimidazol-2-yl)-3,5-dimethylpyrrole-2-carboxamide, and 4-(diphenylmethoxy)-1-[3-(2H-tetrazol-5-yl)propyl]piperidine.

CITATION LIST

Patent Literature

PTL 1: WO2010/104024

PTL 2: WO2007/007778

PTL 3: WO95/01350

Non-Patent Literature

NPL 1: Baumgartner et al., Am J Epidemiol. 1998; 147: 755-63.

NPL 2: Dam et al., J Gerontol A Biol Sci Med Sci. 2014; 69: 584-90.

SUMMARY OF INVENTION

Technical Problem

An object of the present invention is to provide a novel preventive and/or therapeutic agent for sarcopenia.

Solution to Problem

The present inventors conducted repeated studies on preventive and therapeutic methods for sarcopenia, and found that the administration of a prostaglandin D2 production inhibitor can prevent and treat sarcopenia. The inventors conducted further studies based on such findings. The present invention has thus been accomplished.

More specifically, the present invention encompasses the following embodiments.

Item 1. A preventive and/or therapeutic agent for sarcopenia comprising a prostaglandin D2 production inhibitor as an active ingredient.

Item 2. The preventive and/or therapeutic agent according to Item 1, wherein the prostaglandin D2 production inhibitor is an H-PGDS inhibitor.

Item 3. The preventive and/or therapeutic agent according to Item 1 or 2, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide, N-methoxy-N-methyl-4-(5-benzoylbenzimidazol-2-yl)-3,5-dimethylpyrrole-2-carboxamide, 4-(diphenylmethoxy)-1-[3-(2H-tetrazol-5-yl)propyl]piperidine, N-(4-(3-(2-(1H-1,2,4-triazol-1-yl)ethyl)pyrrolidin-1-yl)phenyl)-4-(pyridin-2-ylmethylene)piperidine-1-carboxamide, or 4-((1-methylpyrrol-2-yl)-carbonyl)-N-(1-(4-(2-(1H-1,2,3-triazol-1-yl)-ethyl)-phenyl)-piperidin-4-yl)-1-piperazine carboxamide.

Item 4. The preventive and/or therapeutic agent according to Item 3, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide.

Item 5. A pharmaceutical composition for preventing and/or treating sarcopenia, comprising a prostaglandin D2 production inhibitor.

Item 6. The pharmaceutical composition according to Item 5, wherein the prostaglandin D2 production inhibitor is an H-PGDS inhibitor.

Item 7. The pharmaceutical composition according to Item 5 or 6, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide, N-methoxy-N-methyl-4-(5-benzoylbenzimidazol-2-yl)-3,5-dimethylpyrrole-2-carboxamide, 4-(diphenylmethoxy)-1-[3-(2H-tetrazol-5-yl)propyl]piperidine, N-(4-(3-(2-(1H-1,2,4-triazol-1-yl)ethyl)pyrrolidin-1-yl)phenyl)-4-(pyridin-2-ylmethylene)piperidine-1-carboxamide, or 4-((1-methylpyrrol-2-yl)-carbonyl)-N-(1-(4-(2-(1H-1,2,3-triazol-1-yl)-ethyl)-phenyl)-piperidin-4-yl)-1-piperazine carboxamide.

Item 8. The pharmaceutical composition according to Item 7, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide.

Item 9. A preventive and/or therapeutic method for sarcopenia, comprising administering an effective amount of a prostaglandin D2 production inhibitor.

Item 10. The preventive and/or therapeutic method according to Item 9, wherein the prostaglandin D2 production inhibitor is an H-PGDS inhibitor.

Item 11. The preventive and/or therapeutic method according to Item 9 or 10, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide, N-methoxy-N-methyl-4-(5-benzoylbenzimidazol-2-yl)-3,5-dimethylpyrrole-2-carboxamide, 4-(diphenylmethoxy)-1-[3-(2H-tetrazol-5-yl)propyl]piperidine, N-(4-(3-(2-(1H-1,2,4-triazol-1-yl)ethyl)pyrrolidin-1-yl)phenyl)-4-(pyridin-2-ylmethylene)piperidine-1-carboxamide, or 4-((1-methylpyrrol-2-yl)-carbonyl)-N-(1-(4-(2-(1H-1,2,3-triazol-1-yl)-ethyl)-phenyl)-piperidin-4-yl)-1-piperazine carboxamide.

Item 12. The preventive and/or therapeutic method according to Item 11, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide.

Item 13. A prostaglandin D2 production inhibitor for use in the prevention and/or treatment of sarcopenia.

Item 14. The prostaglandin D2 production inhibitor according to Item 13, wherein the prostaglandin D2 production inhibitor is an H-PGDS inhibitor.

Item 15. The prostaglandin D2 production inhibitor according to Item 13 or 14, which is 4-{(1-methyl-1H-pyrrol-2-yl)carbonyl}-N-[4-{4-(4-morpholinylcarbonyl)-1-piperidinyl}phenyl]-1-piperazine carboxamide, N-methoxy-N-methyl-4-(5-benzoylbenzimidazol-2-yl)-3,5-dimethylpyrrole-2-carboxamide, 4-(diphenylmethoxy)-1-[3-(2H-tetrazol-5-yl)propyl]piperidine, N-(4-(3-(2-(1H-1,2,4-triazol-1-yl)ethyl)pyrrolidin-1-yl)phenyl)-4-(pyridin-2-ylmethylene)piperidine-1-carboxamide, or 4-((1-methylpyrrol-2-yl)-carbonyl)-N-(1-(4-(2-(1H-1,2,3-triazol-1-yl)-ethyl)-phenyl)-piperidin-4-yl)-1-piperazine carboxamide.

Item 16. The prostaglandin D2 production inhibitor according to Item 15, which is 4-{(1-methyl-1H-pyrrol-2-yl)carbonyl}-N-[4-{4-(4-morpholinylcarbonyl)-1-piperidinyl}phenyl]-1-piperazine carboxamide.

Item 17. Use of a prostaglandin D2 production inhibitor in the manufacture of a preventive and/or therapeutic agent for sarcopenia.

Item 18. The use according to Item 17, wherein the prostaglandin D2 production inhibitor is an H-PGDS inhibitor.

Item 19. The use according to Item 17 or 18, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide, N-methoxy-N-methyl-4-(5-benzoylbenzimidazol-2-yl)-3,5-dimethylpyrrole-2-carboxamide, 4-(diphenylmethoxy)-1-[3-(2H-tetrazol-5-yl)propyl]piperidine, N-(4-(3-(2-(1H-1,2,4-triazol-1-yl)ethyl)pyrrolidin-1-yl)phenyl)-4-(pyridin-2-ylmethylene)piperidine-1-carboxamide, or 4-((1-methylpyrrol-2-yl)-carbonyl)-N-(1-(4-(2-(1H-1,2,3-triazol-1-yl)-ethyl)-phenyl)-piperidin-4-yl)-1-piperazine carboxamide.

Item 20. The use according to Item 19, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide.

Advantageous Effects of Invention

The present invention is capable of effectively preventing and treating sarcopenia with almost no side effects.

DESCRIPTION OF EMBODIMENTS

Figure 1:
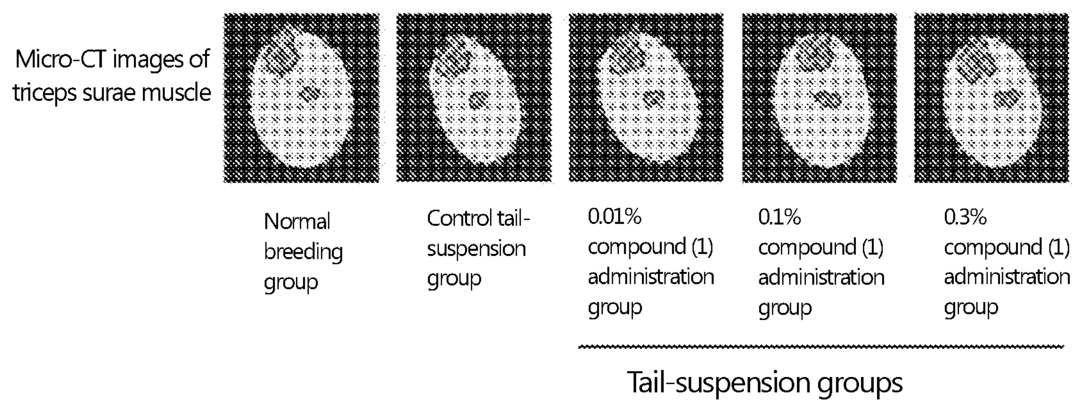
FIG. 1 shows micro-CT images of the triceps surae muscle of tail-suspended mice.

The present invention relates to a preventive and/or therapeutic agent for sarcopenia, comprising a prostaglandin D2 production inhibitor as an active ingredient.

(i) Prostaglandin D2 Production Inhibitor

In the present invention, the “prostaglandin D2 production inhibitor” is not particularly limited as long as it is a drug that inhibits the synthesis of prostaglandin D2 (sometimes referred to in this specification as “PGD2”).

PGD2 is an inflammatory mediator that is produced and released in the largest amount by mast cells activated by binding of a complex of antigens and immunoglobulin E. PGD2 participates in the onset and exacerbation of various diseases, including allergies, and in the regulatory mechanisms of the body.

Synthases that generate PGD2 are referred to as "prostaglandin D synthases", and two different types, hematopoietic prostaglandin D synthase and lipocalin-type prostaglandin D synthase, are known to exist. Human hematopoietic prostaglandin D synthases (H-PGDS) are mainly distributed throughout the placenta, lungs, fetus liver, lymph nodes, brain, heart, thymus, bone marrow, and spleen. At the cellular level, they are reported to be expressed in microglia cells in the brain, bone marrow megakaryocyte, and many kinds of antigen-presenting cells such as Langerhans cells in the skin; Kupffer cells in the liver; macrophages; and dendritic cells, mast cells, and Th2 cells.

The PGD2 production inhibitor of the present invention may inhibit the synthetic activity of hematopoietic prostaglandin D synthase or lipocalin-type prostaglandin D synthase. From the viewpoint of preventing and/or treating sarcopenia, which causes symptoms in muscles, the inhibitor of the present invention is preferably a drug that inhibits the synthesis of PGD2 by hematopoietic prostaglandin D synthase (H-PGDS) (H-PGDS inhibitor).

The PGD2 production inhibitor of the present invention may be a small molecule compound targeting prostaglandin D synthases, a specific antibody against prostaglandin D synthases (e.g., an antibody capable of inhibiting the synthase activity of prostaglandin D synthase), an antisense oligonucleotide against prostaglandin D synthases, an aptamer, or the like.

Examples of the PGD2 production inhibitor include 4-{(1-methyl-1H-pyrrol-2-yl)carbonyl}-N-[4-{4-(4-morpholinylcarbonyl)-1-piperidinyl}phenyl]-1-piperazine carboxamide represented by the following chemical formula (which may be referred to in this specification as "compound (1)"):

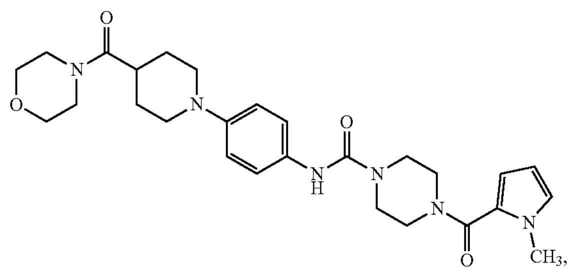 [SMILES: Cn1cccc1C(=O)N1CCN(C(=O)Nc2ccc(N3CCC(C(=O)N4CCOCC4)CC3)cc2)CC1]

4-(diphenylmethoxy)-1-[3-(2H-tetrazol-5-yl)propyl]piperidine represented by the following chemical formula (which may be referred to in this specification as "compound (2)"):

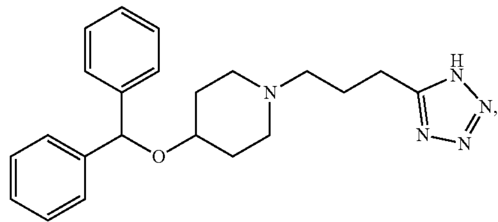 [SMILES: c1ccc(C(OC2CCN(CCCc3nnn[nH]3)CC2)c2ccccc2)cc1]

N-methoxy-N-methyl-4-(5-benzoylbenzimidazol-2-yl)-3,5-dimethylpyrrole-2-carboxamide represented by the following chemical formula (which may be referred to in this specification as "compound (3)"):

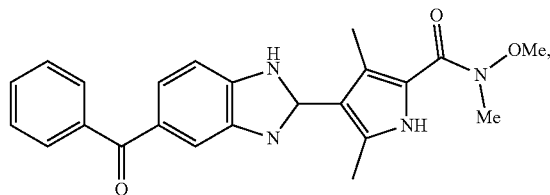 [SMILES: CON(C)C(=O)c1[nH]c(C)c(C2Nc3ccc(C(=O)c4ccccc4)cc3N2)c1C]

N-(4-(3-(2-(1H-1,2,4-triazol-1-yl)ethyl)pyrrolidin-1-yl)phenyl)-4-(pyridin-2-ylmethylene)piperidine-1-carboxamide represented by the following chemical formula (which may be referred to in this specification as "compound (4)"):

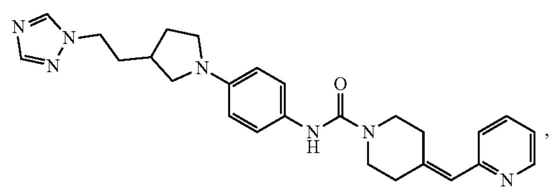 [SMILES: O=C(Nc1ccc(N2CCC(CCn3cncn3)C2)cc1)N1CCC(=Cc2ccccn2)CC1]

4-((1-methylpyrrol-2-yl)-carbonyl)-N-(1-(4-(2-(1H-1,2,3-triazol-1-yl)-ethyl)-phenyl)-piperidin-4-yl)-1-piperazine carboxamide represented by the following chemical formula (which may be referred to in this specification as "compound (5)"):

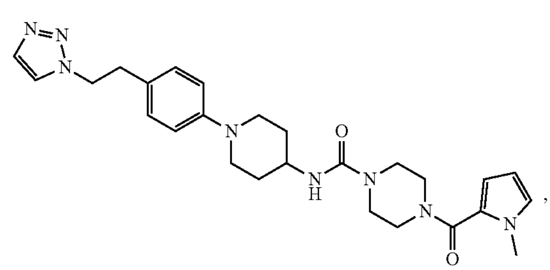 [SMILES: Cn1cccc1C(=O)N1CCN(C(=O)NC2CCN(c3ccc(CCn4ccnn4)cc3)CC2)CC1]

and the like, and pharmaceutically acceptable salts thereof, with 4-{(1-methyl-1H-pyrrol-2-yl)carbonyl}-N-[4-{4-(4-morpholinylcarbonyl)-1-piperidinyl}phenyl]-1-piperazine carboxamide being preferable.

The phrase "pharmaceutically acceptable salt" refers to salts that exhibit a desired pharmacological activity of the compounds, and that are prepared from pharmaceutically acceptable non-toxic bases or acids including, inorganic or organic bases and inorganic or organic acids.

Specific examples of such salts include acid addition salts with inorganic acids, such as hydrochloric acid, hydrobromic acid, hydroiodic acid, sulfuric acid, nitric acid, and phosphoric acid; acid addition salts with organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, paratoluenesulfonic acid, and glutamic acid; salts with inorganic bases, such as sodium, potassium, magnesium, calcium, and aluminum; salts with organic bases, such as methylamine, ethylamine, meglumine, and ethanolamine; salts with basic amino acids, such as lysine, arginine, and ornithine; and ammonium salts.

The PGD2 production inhibitor of the present invention can be produced by a known organic synthesis method. For example, 4-{(1-methyl-1H-pyrrol-2-yl)carbonyl}-N-[4-{4-

(4-morpholinylcarbonyl)-1-piperidinyl}phenyl]-1-piperazine carboxamide can be produced in accordance with the method disclosed in WO2010/104024. N-Methoxy-N-methyl-4-(5-benzoylbenzimidazol-2-yl)-3,5-dimethylpyrrole-2-carboxamide can be produced in accordance with the method disclosed in WO2007/007778. 4-(Diphenylmethoxy)-1-[3-(2H-tetrazol-5-yl)propyl]piperidine can be produced in accordance with the method disclosed in WO95/01350. N-(4-(3-(2-(1H-1,2,4-Triazol-1-yl)ethyl)pyrrolidin-1-yl)phenyl)-4-(pyridin-2-ylmethylene)piperidine-1-carboxamide can be produced in accordance with the method disclosed in WO2012/033069. 4-((1-Methylpyrrol-2-yl)-carbonyl)-N-(1-(4-(2-(1H-1,2,3-triazol-1-yl)-ethyl)-phenyl)-piperidin-4-yl)-1-piperazine carboxamide can be produced in accordance with the method disclosed in WO2011/090062.

(ii) Sarcopenia

Sarcopenia is a disease characterized by progressive and systemic skeletal muscle mass loss and muscle strength loss. The European working group on sarcopenia in older people (EWGSOP) has proposed classifying sarcopenia into "pre-sarcopenia," which is characterized by only a decrease in the amount of muscle, "sarcopenia," which is characterized by two findings, i.e., muscle amount decrease and muscle strength loss or physical performance deterioration, and "severe sarcopenia," which is characterized by three findings, i.e., muscle amount decrease, muscle strength loss, and physical performance deterioration. The term "sarcopenia" as used in this specification includes pre-sarcopenia, sarcopenia, and severe sarcopenia.

Sarcopenia includes primary (age-related) sarcopenia with no apparent cause other than aging, and secondary sarcopenia with one or more apparent causes other than aging. Secondary sarcopenia is categorized into three main causes, i.e., a decrease in activity, diseases (e.g., those associated with severe organ failure, inflammatory diseases, malignant tumors, or endocrine diseases), and insufficient intake of nutrients. Secondary sarcopenia includes disuse muscle atrophy, which occurs when muscle is not used for a long period of time due to hospitalization etc.

Due to the difference in onset mechanisms, sarcopenia is distinguished from various myopathies, such as acquired myopathies and hereditary myopathies, which cause symptoms in muscle. Specific examples of acquired myopathies include myositis. Specific examples of hereditary myopathies include muscular dystrophy. Myopathies are progressive intractable diseases in which muscle strength is reduced due to muscle atrophy, and often develop at a young age, like Duchenne muscular dystrophy, which is a typical disease. On the other hand, sarcopenia is a disease caused by a negative balance between muscle synthesis and degradation, leading to a decrease in the amount of muscle. It is believed that there is no direct genetic cause in sarcopenia, as in the dystrophin gene mutation in Duchenne muscular dystrophy. Inflammatory myopathies, such as myositis, are diseases in which inflammation is caused specifically in muscle itself. Sarcopenia, on the other hand, can develop in association with inflammatory diseases in tissues other than muscle (e.g., rheumatoid arthritis, pulmonary tuberculosis, and inflammatory bowel disease).

(iii) Preventive Agent and Therapeutic Agent

The term "treatment" or "therapeutic" as used in this specification generally means a cure or amelioration of symptoms associated with sarcopenia, or suppression of the symptoms. The term "prevention" or "preventive" means preventing the onset of symptoms associated with sarcopenia.

The preventive agent and therapeutic agent of the present invention may consist only of a PGD2 production inhibitor, which is an active ingredient. The preventive agent and therapeutic agent also can further comprise a pharmaceutical carrier, and the like, in addition to the PGD2 production inhibitor as an active ingredient. Accordingly, the preventive agent and therapeutic agent of the present invention can be prepared as a pharmaceutical composition consisting of a single component or containing two or more components.

The preventive agent and therapeutic agent of the present invention can be produced as various dosage formulations by a known method optionally using a pharmaceutically acceptable carrier. The administration may be oral or parenteral. Examples of the formulation form include, but are not particularly limited to, oral agents, such as tablets, coated tablets, pills, powders, granules, capsules, liquids, suspensions, and emulsions; and parenteral agents, such as injections, suppositories, and inhalants.

In preparing tablets, examples of carriers include excipients, such as lactose, sucrose, sodium chloride, glucose, urea, starch, calcium carbonate, kaolin, crystalline cellulose, or silicic acid; binders, such as water, ethanol, propanol, cornstarch, simple syrup, glucose solution, starch solution, gelatin solution, carboxymethylcellulose, shellac, methylcellulose, hydroxypropylcellulose, hydroxypropylmethylcellulose, potassium phosphate, or polyvinyl pyrrolidone; disintegrants, such as dry starch, sodium alginate, powdered agar, powdered laminaran, sodium hydrogencarbonate, calcium carbonate, polyoxyethylene sorbitan fatty acid ester, sodium lauryl sulfate, stearic acid monoglyceride, or lactose; disintegration inhibitors, such as sucrose, stearic acid, cacao butter, or hydrogenated oils; absorbefacients, such as quaternary ammonium salts or sodium lauryl sulfate; moisturizers, such as glycerin or starch; adsorbents, such as starch, lactose, kaolin, bentonite, or colloidal silicic acid; and lubricants, such as purified talc, stearate, boric acid powder, or polyethylene glycol. Further, the tablets may be tablets optionally coated with a usual coating, such as sugar-coated tables, gelatin-coated tablets, enteric-coated tablets, film-coated tablets, double-coated tablets, or multi-coated tablets.

In preparing pills, examples of the carrier include excipients, such as glucose, lactose, starch, cacao butter, hardened vegetable oil, kaolin, or talc; binders, such as gum arabic powder, tragacanth powder, gelatin, or ethanol; and disintegrators, such as laminaran or agar. Capsules are usually prepared in a standard method by mixing the drug with one or more carriers given as examples above, and encapsulating the mixture into hard gelatin capsules, soft capsules, etc.

In preparing oral liquid formulations, an internal liquid medicine, a syrup, an elixir, or the like may be prepared by a standard method using a sweetening/flavoring agent, buffer, stabilizer, etc. In this case, examples of sweetening/flavoring agents include sucrose, orange peel, citric acid, and tartaric acid; examples of buffers include sodium citrate; and examples of stabilizers include tragacanth, gum arabic, and gelatin.

In preparing suppositories, examples of usable carriers include polyethylene glycol, cacao butter, higher alcohols, esters of higher alcohols, gelatin, and semisynthetic glycerides.

In preparing injections, the liquids, emulsions, and suspensions are preferably sterilized and rendered isotonic to the blood. Examples of diluents for preparing such dosage forms include water, aqueous lactic acid solution, ethyl alcohol, propylene glycol, macrogols, ethoxylated isostearyl alcohol, polyoxyethylenated isostearyl alcohol, and polyoxyethylene sorbitan fatty acid ester.

In this case, sodium chloride, glucose, or glycerin in an amount sufficient to prepare an isotonic solution may be added to the pharmaceutical formulation. Further, usual solubilizers, buffers, anesthetics, and the like, may also be added to the pharmaceutical formulation.

In preparing inhalants, various forms, such as an aerosol, a powdered inhalant, and a liquid inhalant, can be used.

Additionally, coloring agents, preservatives, aromatics, flavors, sweetening agents, or other medicinal products may be incorporated, if necessary, into the pharmaceutical formulation.

The daily dose refers to an amount of active ingredient to be administered daily. In the preventive agent and therapeutic agent of the present invention, the daily dose of the PGD2 production inhibitor on the day of administration varies depending on the patient's symptoms, weight, age, sex, etc., and cannot be determined unconditionally. From the viewpoint of the prevention and/or therapeutic effect on sarcopenia, the dose is usually preferably 50 to 4000 mg/day, more preferably 100 to 4000 mg/day, and even more preferably 400 to 1600 mg/day in an adult (body weight: 50 kg). Further, the PGD2 production inhibitor is preferably administered so that the blood concentration of the patient after administration is preferably 1000 to 800000 ng·hr/mL, and more preferably 1500 to 40000 ng·hr/mL.

Further, the amount of the prostaglandin D2 production inhibitor to be incorporated in each of the above dosage unit forms varies depending on the symptoms of the patient to which the inhibitor is applied or depending on its dosage form etc. Generally, the amount per dosage unit form is preferably 0.05 to 1000 mg for an oral agent, 0.01 to 500 mg for an injection, and 1 to 1000 mg for a suppository.

The preventive agent and therapeutic agent of the present invention are appropriately determined according to the formulation form, age, sex, other conditions of the patient, the severity of the symptoms of the patient, and the like. For example, tablets, pills, powders, granules, capsules, liquids, suspensions, and emulsions are orally administered. Injections are intravenously administered singly, or as a mixture with a general infusion liquid, such as liquid glucose or an amino acid liquid. Further, as necessary, the injections are singly administered intra-arterially, intramuscularly, intradermally, subcutaneously, or intraperitoneally. Suppositories are intrarectally administered.

Examples of the subject of administration of the preventive or therapeutic agent of the present invention include mammals, such as humans, monkeys, mice, rats, rabbits, dogs, cats, cattle, horses, pigs, and sheep.

The age of the subject to which the preventive or therapeutic agent of the present invention is administered is not particularly limited. To treat primary (age-related) sarcopenia in people, the person may be 60 or older, at which age there is a higher tendency of developing primary (age-related) sarcopenia with age, and the person is more preferably 70 or older, and even more preferably 80 or older. On the other hand, secondary sarcopenia, which includes disuse muscle atrophy, may develop in people at all ages, in addition to the elderly, and the age of the subject of administration is not limited.

The present invention includes the following embodiments.

- A preventive and/or therapeutic agent for sarcopenia, comprising a prostaglandin D2 production inhibitor as an active ingredient.
- A pharmaceutical composition for preventing and/or treating sarcopenia, comprising a prostaglandin D2 production inhibitor.
- A preventive and/or therapeutic method for sarcopenia, comprising administering an effective amount of a prostaglandin D2 production inhibitor to a subject in need thereof.
- A prostaglandin D2 production inhibitor for use in the prevention and/or treatment of sarcopenia.
- Use of a prostaglandin D2 production inhibitor in the manufacture of a preventive and/or therapeutic agent for sarcopenia.

EXAMPLES

The present invention is described below in more detail with reference to Test Examples; however, the present invention is not limited to these.

Test Example 1

Evaluation of Inhibition of Muscular Atrophy in Tail-Suspended Mice—Part 1

Eight-week-old C57/BL6J male mice (Japan SLC, Inc., Shizuoka, Japan) were subjected to tail-suspension to obtain mice model with disuse muscle atrophy of their lower limbs.

The tail-suspension was performed according to the description in Skelet Muscle. 2015; 5:34. Specifically, the tail of a mouse was fixed so that the hind limbs of the mouse did not touch the ground, and this state was maintained for about 2 weeks. Tail-suspension is known to cause skeletal muscle mass loss and muscle strength loss in the hind limbs, whereby an experimental model with disuse muscle atrophy, which is one type of sarcopenia, can be produced.

During the period of tail-suspension, feed containing 0.01, 0.1, or 0.3 mass % compound (1) was fed for 2 weeks (compound (1) administration groups). As control groups, a normal breeding group, which was not subjected to the tail-suspension, as well as a control tail-suspension group, which was fed with feed that did not contain the compound, were prepared. The number of tests was n=8 in each group.

Two weeks after the initiation of the experiment (the initiation of the tail-suspension and the initiation of feeding of the feed that contained the compound), micro-CT (micro-computed tomography) imaging of the mouse hind limbs was performed. The muscle volume at the periphery of the tibia (triceps surae muscle) was measured using 3D volumetric analysis software. Micro-CT imaging was performed using a microfocus X-ray CT system (micro-CT: SMX-90T manufactured by Shimadzu Corporation). FIG. 1 shows examples of micro-CT images.

Figure 2:
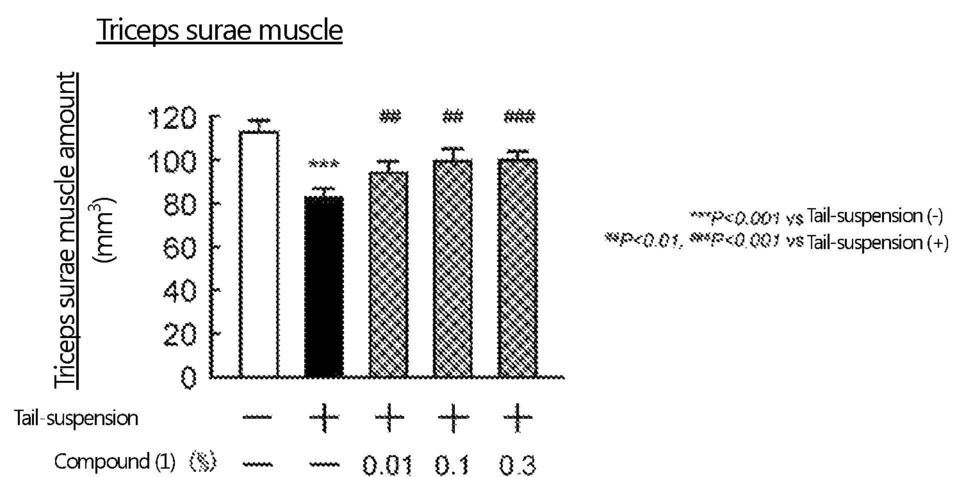
FIG. 2 is a graph showing the results of the measurement of muscle volume in tail-suspended mice.

The midpoint of the fibula in the lower limb of each mouse was determined using 3D images created from the micro-CT images, and the volume of total muscle mass at the measurement area starting from the midpoint was measured. The lower leg includes the gastrocnemius muscle, soleus muscle, tibialis anterior muscle, and extensor digitorum longus muscle. The triceps surae muscle refers to the gastrocnemius muscle and the soleus muscle. FIG. 2 shows the results.

Figure 3:
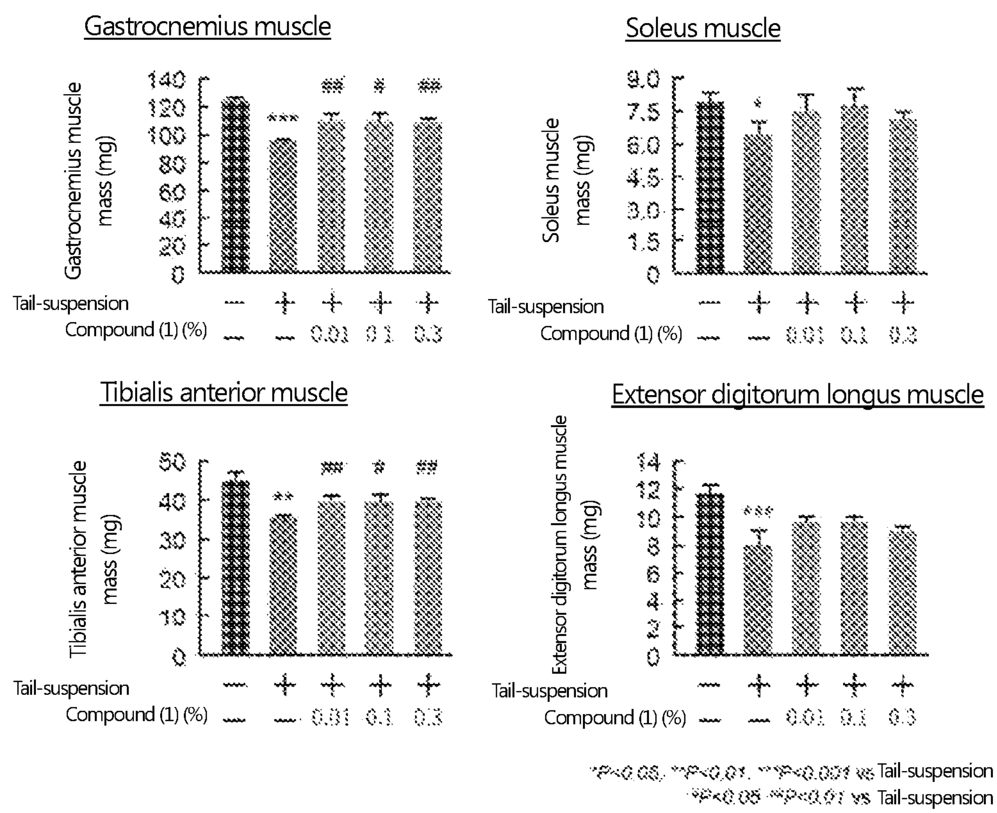
FIG. 3 is graphs showing the results of the measurement of muscle mass in tail-suspended mice.

Furthermore, the gastrocnemius muscle, soleus muscle, tibialis anterior muscle, and extensor digitorum longus muscle were collected from the mouse hind limbs after tail-suspension, and the wet mass (muscle mass) of each muscle was measured. FIG. 3 shows the results.

According to the results shown in FIG. 2, the control tail-suspension group, which was subjected to tail suspension, showed considerable muscle mass loss, while the compound administration groups, which were fed with the mixed feed of compound (1), showed significant suppression of muscle mass loss.

According to the results shown in FIG. 3, the control tail-suspension group showed muscle mass loss in all of the hind limb muscles, while the compound administration groups showed a tendency to suppress a decrease in the muscle amount in all of the hind limb muscles.

Figure 4:
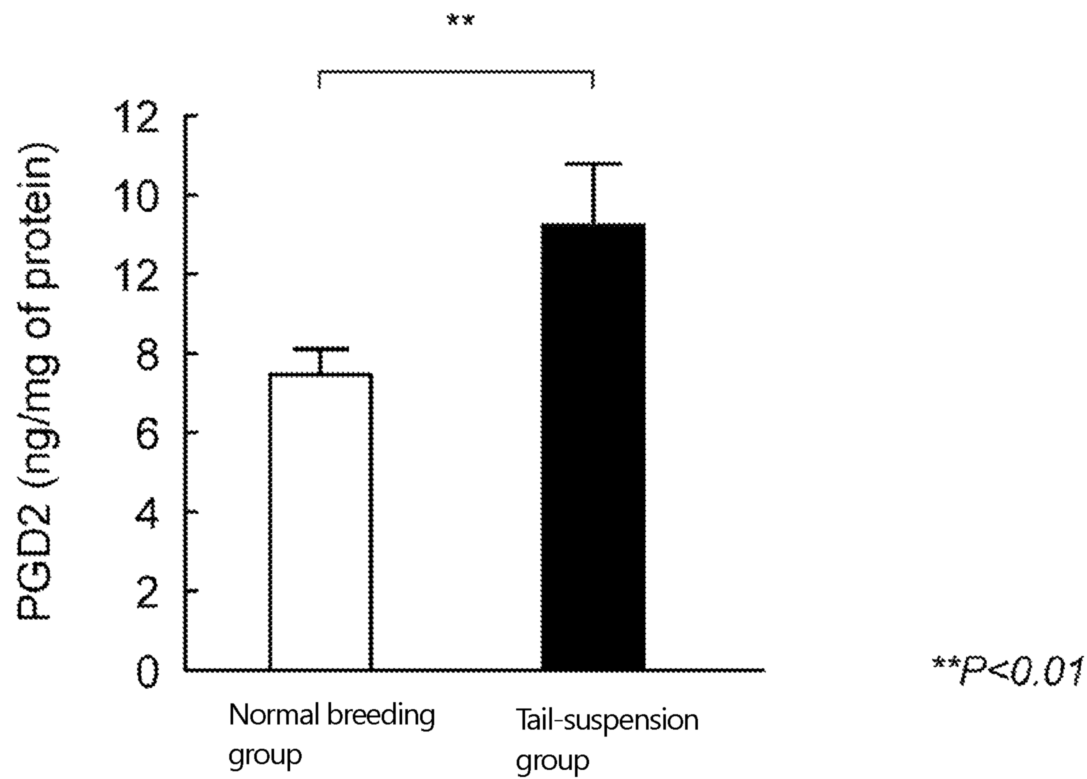
FIG. 4 is a graph showing the prostaglandin D2 content in tail-suspended mice.

Furthermore, the gastrocnemius muscle collected from the mouse lower limb after tail-suspension was rapidly frozen, and PBS was added thereto, followed by disruption using a homogenizer. The disrupted liquid was centrifuged (4° C., 15,000 rpm) for 10 minutes, and the supernatant was collected. The concentration of PGD2 contained in the supernatant was measured by the ELISA method (Prostaglandin D2 ELISA, manufactured by Cayman Chemical Company). The measurement results of the ELISA method were corrected based on the total protein concentration of the supernatant, and the content of PGD2 per 1 mg of protein in the muscle (ng/mg of protein) was determined. FIG. 4 shows the results. The results revealed that the tail-suspension promoted the PGD2 production in skeletal muscle.

A Student's t-test was used for the significant difference test. In the figures, *, , and * respectively indicate $P<0.05$, $P<0.01$, and $P<0.001$ for the normal breeding group (tail-suspension (−)), which was not subjected to the tail-suspension. #, ##, and ### respectively indicate $P<0.05$, $P<0.01$, and $P<0.001$ for the control tail-suspension group (tail-suspension (+)), which was fed with feed that did not contain the compound.

The preventive and therapeutic effects of the compound of the present invention can be verified by initiating feeding the mixed feed that contained compound (1) at the same time as the tail-suspension was performed. The results shown in FIGS. 1 to 3 above clarified the preventive effect and therapeutic effect of compound (1) of the present invention on muscle mass loss and on a decrease in the muscle amount.

Test Example 2

Evaluation of Blood Kinetics of Compound in Mice

Mixed feed that contained 0.01, 0.1, or 0.3 mass % compound (1) were fed to 7-week-old C57BL/6 mice (male, Charles River Japan Ltd., weight: 20.7-23.7 g) for 13 days.

Blood was collected from the face by using an animal lancet at 10 a.m., 1, 5, and 9 p.m. on day 12 and 10 a.m. on day 13.

About 75 μL of blood was collected into a heparin-coated hematocrit tube. The concentration of the compound in the plasma after centrifugation was measured using liquid chromatography-mass spectrometry (LC/MS). Table 1 shows the measurement results. The results confirmed that feeding of the mixed feed that contained compound (1) achieved a dose-dependent increase in the compound concentration in blood in the range of 0.01 mass % to 0.3 mass %.

Since a mouse with a body weight of about 20 g consumes about 4 g of the feed per day (spilling of food is not assumed), the daily intake of the compound is estimated to be 0.4 mg (0.01 mass % mixed feed), 4 mg (0.1 mass % mixed feed), or 12 mg (0.3 mass % mixed feed). The body weight conversion values were 20 mg/kg (0.01 mass % mixed feed), 200 mg/kg (0.1 mass % mixed feed), and 600 mg/kg (0.3 mass % mixed feed).

TABLE 1

| | Cmax (μM) | $AUC_{0-24\ h}$ (μM*h) |
|---|---|---|
| 0.01% mixed feed | 0.23 | 4.29 |
| 0.1% mixed feed | 2.21 | 38.31 |
| 0.3% mixed feed | 6.41 | 103.68 |

Test Example 3

Evaluation of Inhibition of Muscular Atrophy in Tail-Suspended Mice—Part 2

Eight-week-old C57/BL6J male mice (Japan SLC, Inc., Shizuoka, Japan) were subjected to the tail-suspension to obtain mice model with disuse muscle atrophy of their lower limbs.

While the tail-suspension was performed, feed containing 0.01 mass % compound (1), compound (2), compound (3), compound (4), or compound (5) was fed for 2 weeks (compound (1) administration group, compound (2) administration group, compound (3) administration group, compound (4) administration group, and compound (5) administration group). As control groups, a normal breeding group, which was not subjected to the tail-suspension, as well as a control tail-suspension group, which was fed with feed that did not contain the compounds, were prepared. The number of tests was n=8 in each group.

Figure 5:
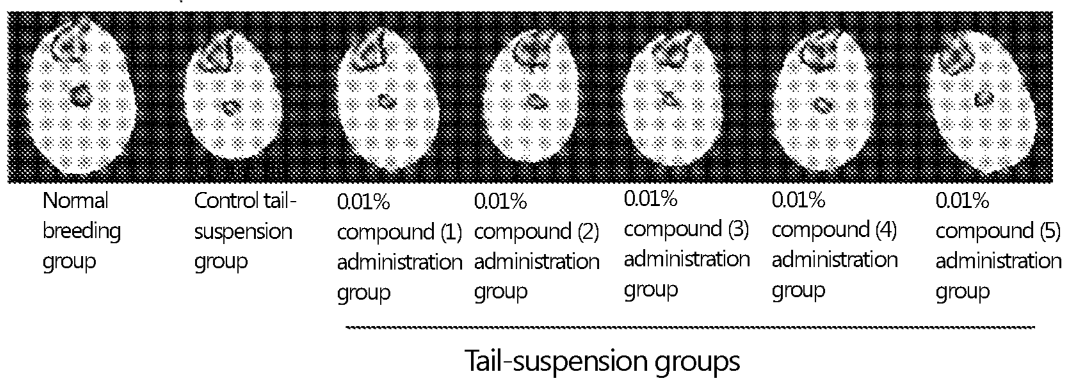
FIG. 5 is micro-CT images of the triceps surae muscle of tail-suspended mice.

Two weeks after the initiation of the experiment (the initiation of the tail-suspension and the initiation of feeding with the feed that contained the compounds), micro-CT imaging of the mouse hind limbs was performed. The muscle volume at the periphery of the tibia (triceps surae muscle) was measured using 3D volumetric analysis software. Micro-CT imaging was performed using a microfocus X-ray CT system (micro-CT: SMX-90T, manufactured by Shimadzu Corporation). FIG. 5 shows examples of micro-CT images.

Figures 6, 7:
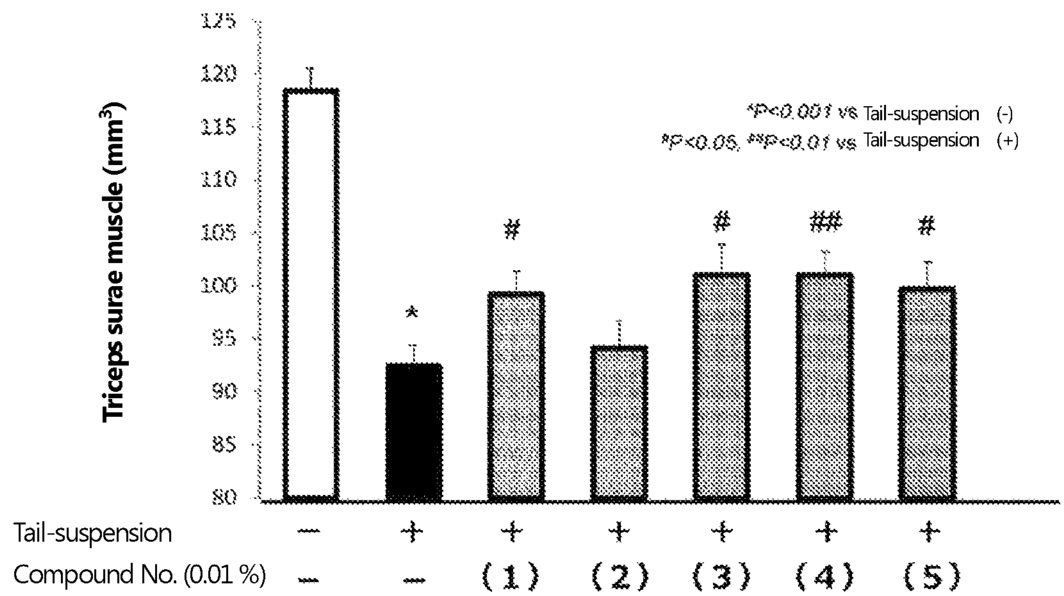
FIG. 6 is a graph showing the results of the measurement of muscle volume in tail-suspended mice.
FIG. 7 is a table showing the rate of increase in muscle volume in tail-suspended mice.

The midpoint of the fibula in the lower limb of each mouse was determined using 3D images created from the micro-CT images, and the volume of total muscle mass at the measurement area starting from the midpoint was measured. FIG. 6 shows the results. FIG. 7 shows the rate of increase in the muscle volume, based on the control tail-suspension group. The rate of increase was calculated according to the following: (compound administration group−control tail-suspension group)/(normal breeding group−control tail-suspension group)×100.

Figures 8, 9:
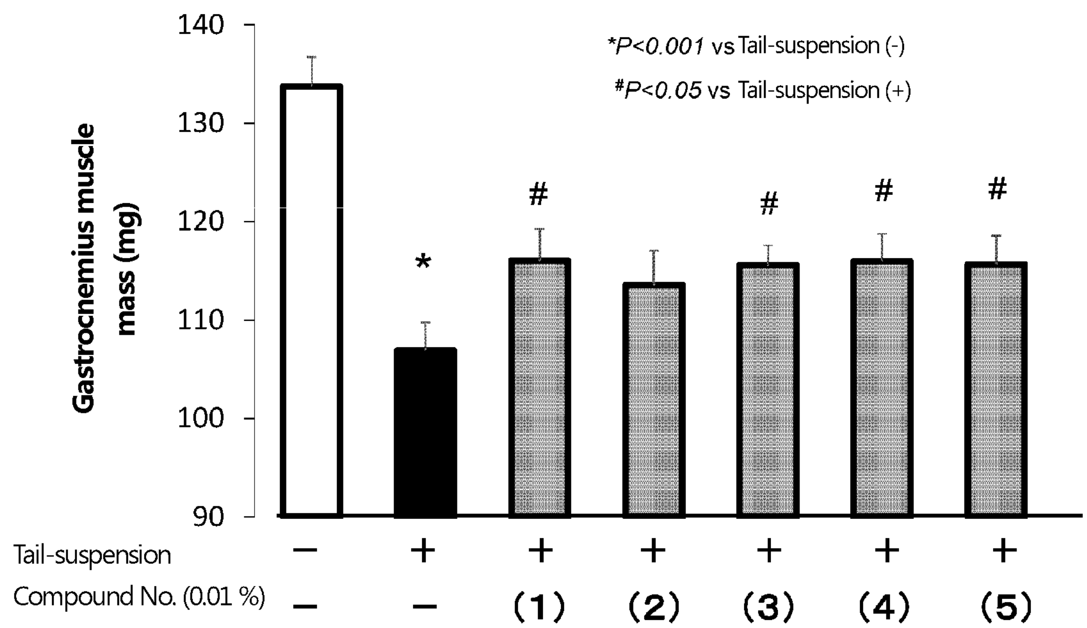
FIG. 8 is a graph showing the results of the measurement of muscle mass in tail-suspended mice.
FIG. 9 is a table showing the rate of increase in muscle mass in tail-suspended mice.

Furthermore, the gastrocnemius muscle was collected from the mouse hind limb after the tail-suspension, and the wet mass (muscle mass) was measured. FIG. 8 shows the results. FIG. 9 shows the rate of increase in the muscle mass, based on the control tail-suspension group. The rate of increase was calculated according to the following: (compound administration group−control tail-suspension group)/(normal breeding group−control tail-suspension group)×100.

According to the results shown in FIG. 6 and FIG. 7, the control tail-suspension group, which was subjected to tail suspension, showed considerable muscle mass loss, while the compound administration groups, which were fed with the mixed feed of compound (1), compound (3), compound (4), or compound (5), showed significant suppression of muscle mass loss. On the other hand, the group that was fed with the mixed feed that contained compound (2) did not show significant suppression of muscle mass loss although a tendency toward suppression was observed.

According to the results shown in FIG. 8 and FIG. 9, the control tail-suspension group showed a decrease in the mass of gastrocnemius muscle while the compound administration groups, which were fed with the mixed feed of compound (1), compound (3), compound (4), or compound (5), showed significant suppression of the decrease in the muscle amount. On the other hand, the group that was fed with the mixed feed that contained compound (2) did not show a significant difference although a tendency toward suppression of the decrease in the muscle amount was observed.

A Student's t-test was used for the significant difference test. In the figures, * indicates $P<0.001$ for the normal breeding group (tail-suspension (−)), which was not subjected to the tail-suspension. # and ## respectively indicate $P<0.05$ and $P<0.01$ for the control tail-suspension group (tail-suspension (+)), which was fed with the feed that did not contain the compounds.

The preventive and therapeutic effects of the compound of the present invention can be verified by initiating feeding the mixed feed that contained the compounds at the same time as the tail-suspension was performed. The results shown in FIGS. 5 to 9 above revealed that compound (1), compound (3), compound (4), and compound (5) showed a significant improvement, and compound (2) also showed a tendency toward improvement. These results clarified the preventive effect and the therapeutic effect of the compounds of the present invention on muscle mass loss and on a decrease in the muscle amount.

Test Example 4

Inhibition of Muscular Atrophy in Tail-Suspended Mice—Part 3

Eight-week-old C57/BL6J male mice (Japan SLC, Inc., Shizuoka, Japan) were subjected to the tail-suspension to obtain mice model with disuse muscle atrophy of their lower limbs.

One week after tail-suspension, feed that contained 0.3 mass % compound (1) was fed for 2 weeks (compound (1) administration group). As control groups, a normal breeding group, which was not subjected to the tail-suspension, as well as a control tail-suspension group, which was fed with feed that did not contain the compound for 3 weeks, were prepared. The number of tests was n=8 in each group.

Figure 10:
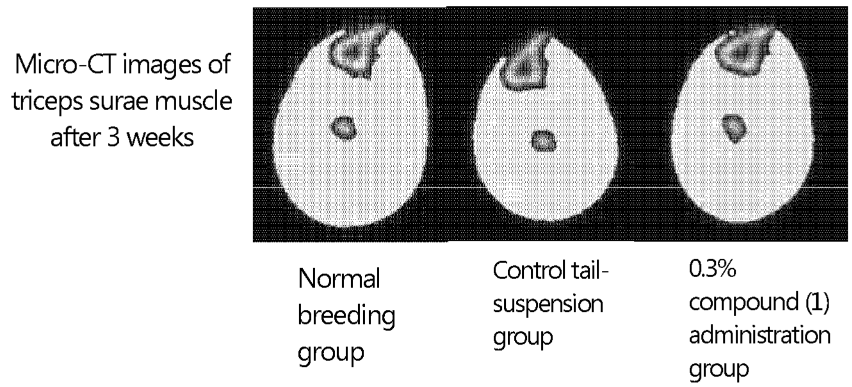
FIG. 10 is micro-CT images of the triceps surae muscle of mice 3 weeks after tail-suspension.

Micro-CT imaging of the mouse hind limbs was performed before tail suspension, 1 week after suspension, 2 weeks after suspension, and 3 weeks after suspension. The muscle volume at the periphery of the tibia (triceps surae muscle) was measured using 3D volumetric analysis software. Micro-CT imaging was performed using a microfocus X-ray CT system (micro-CT: SMX-90T, manufactured by Shimadzu Corporation). FIG. 10 shows examples of micro-CT images 3 weeks after suspension.

Figure 11:
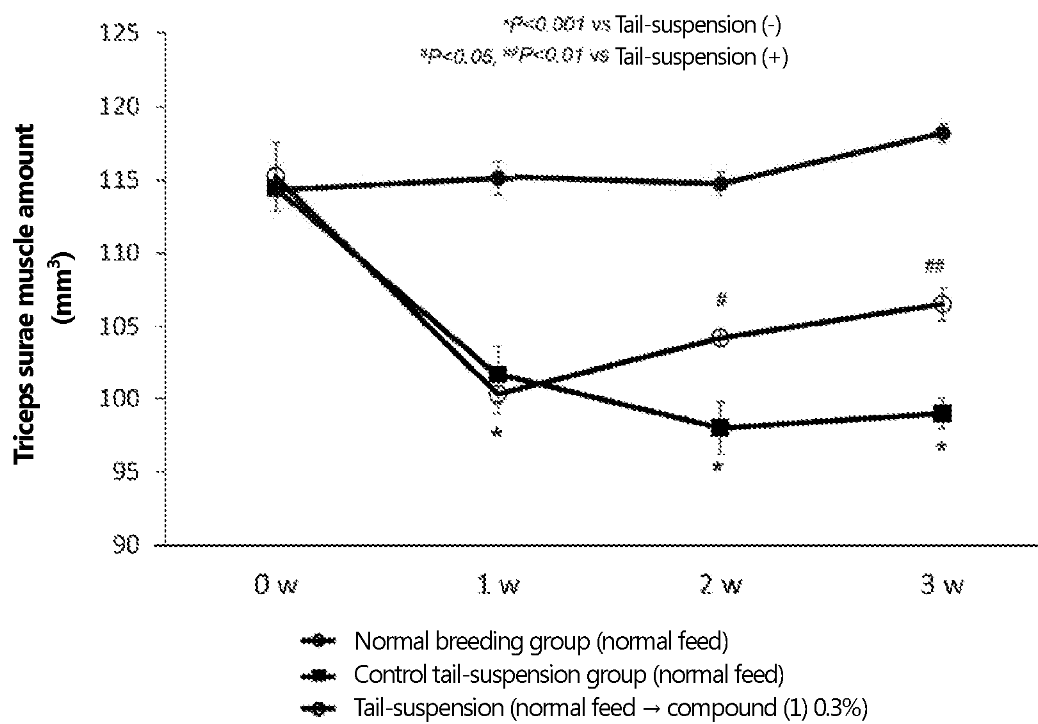
FIG. 11 is a graph showing the results of the measurement of muscle volume changes in tail-suspended mice.

The midpoint of the fibula in the lower limb of each mouse was determined using 3D images created from the micro-CT images, and the volume of total muscle mass at the measurement area starting from the midpoint was measured. FIG. 11 shows the results of the volume change.

Figure 12:
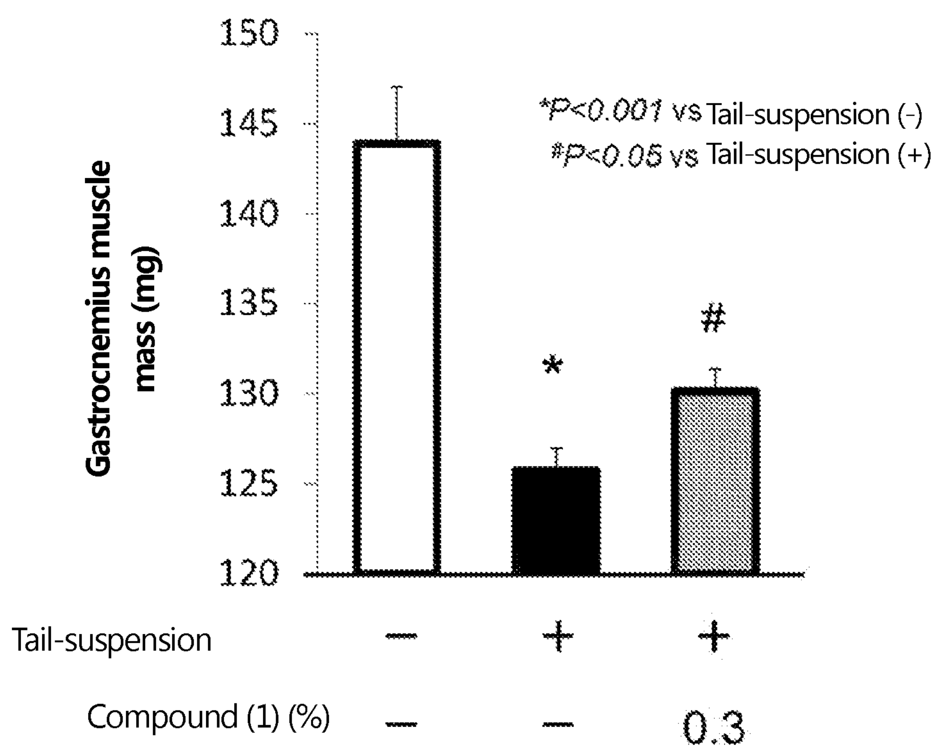
FIG. 12 is a graph showing the results of the measurement of muscle mass in mice 3 weeks after tail-suspension.

Furthermore, the gastrocnemius muscle was collected from the mouse hind limb three weeks after the tail-suspension, and the wet mass (muscle mass) was measured. FIG. 12 shows the results.

According to the results shown in FIG. 11, the control tail-suspension group, which was subjected to tail suspension, showed significant muscle mass loss at week 1 after the tail suspension, and the muscle mass loss was further promoted at week 2, and the loss was maintained at the same level until week 3. On the other hand, the group fed with the mixed feed that contained compound (1) did not show further muscle mass loss at week 1 after the tail-suspension, and the muscle amount showed a tendency toward an increase instead. This group showed a significantly higher muscle amount at week 2 and week 3, compared to the control tail-suspension group; accordingly, the therapeutic effect of compound (1) was confirmed.

According to the results shown in FIG. 12, the control tail-suspension group showed a decrease in the mass of gastrocnemius muscle while the compound administration group, which was fed with the mixed feed of compound (1), showed a significant therapeutic effect on the muscle amount.

A Student's t-test was used for the significant difference test. In the figures, * indicates $P<0.001$ for the normal breeding group (tail-suspension (−)), which was not subjected to the tail-suspension. # and ## respectively indicate $P<0.05$ and $P<0.01$ for the control tail-suspension group (tail-suspension (+)), which was fed with the feed that did not contain the compound.

One week after the initiation of the tail-suspension, considerable muscle mass loss was observed. The therapeutic effect of the compound of the present invention can be verified by initiating feeding the mixed feed that contained compound (1) one week after the initiation of tail suspension. The results shown in FIGS. 10 to 12 clarified the therapeutic effect of compound (1) of the present invention on muscle mass loss and on a decrease in the muscle amount.

The invention claimed is:

1. A method for inhibiting and/or treating sarcopenia, comprising administering to a subject an effective amount of a prostaglandin D2 production inhibitor, wherein the prostaglandin D2 production inhibitor is 4-{(1-methyl-1H-pyrrol-2-yl)carbonyl}-N-[4-{4-(4-morpholinylcarbonyl)-1-piperidinyl}phenyl]-1-piperazine carboxamide.

2. The method according to claim 1, wherein said sarcopenia is primary sarcopenia and/or secondary sarcopenia.

3. The method according to claim 2, wherein said sarcopenia is primary sarcopenia and said subject is 60 years old or older.

4. The method according to claim 2, wherein said secondary sarcopenia is caused by a decrease in activity, disease, insufficient intake of nutrients, and/or disuse muscle atrophy.

5. The method according to claim 3, wherein the subject with primary sarcopenia is 70 years old or older.

6. The method according to claim 5, wherein the subject with primary sarcopenia is 80 years old or older.

* * * * *